United States Patent
Pipino et al.

[11] Patent Number: 5,943,136
[45] Date of Patent: Aug. 24, 1999

[54] INTRA-CAVITY TOTAL REFLECTION FOR HIGH SENSITIVITY MEASUREMENT OF OPTICAL PROPERTIES

[75] Inventors: Andrew C. R. Pipino, Gaithersburg; Jeffrey W. Hudgens, Rockville, both of Md.

[73] Assignee: The United States of America as represented by the Secretary of Commerce, Washington, D.C.

[21] Appl. No.: 08/962,170

[22] Filed: Oct. 31, 1997

[51] Int. Cl.⁶ .................................................. G01N 21/00
[52] U.S. Cl. ........................................... 356/440; 356/439
[58] Field of Search ................................... 356/439, 440, 356/246, 445, 432, 136, 244

[56] References Cited

U.S. PATENT DOCUMENTS 5,437,840  8/1995  King et al. ............................... 356/136
5,528,040  6/1996  Lehmann ................................... 356/439

*Primary Examiner*—Robert H. Kim
*Assistant Examiner*—Amanda Merlino
*Attorney, Agent, or Firm*—Larson & Taylor

[57] ABSTRACT

An optical cavity resonator device is provided for conducting sensitive measurement of optical absorption by matter in any state with diffraction-limited spatial resolution through utilization of total internal reflection within a high-Q (high quality, low loss) optical cavity. Intracavity total reflection generates an evanescent wave that decays exponentially in space at a point external to the cavity, thereby providing a localized region where absorbing materials can be sensitively probed through alteration of the Q-factor of the otherwise isolated cavity. When a laser pulse is injected into the cavity and passes through the evanescent state, an amplitude loss resulting from absorption is incurred that reduces the lifetime of the pulse in the cavity. By monitoring the decay of the injected pulse, the absorption coefficient of manner within the evanescent wave region is accurately obtained from the decay time measurement.

20 Claims, 2 Drawing Sheets

INTRA-CAVITY TOTAL REFLECTION FOR
HIGH SENSITIVITY MEASUREMENT OF
OPTICAL PROPERTIES

FIELD OF THE INVENTION

The present invention relates to matter identifying devices, and more particularly, to those that measure the optical absorption by matter within an evanescent wave field generated by total internal reflection within a low-loss optical cavity.

BACKGROUND OF THE INVENTION

Optical absorption spectroscopy is fundamentally important in chemical analysis, providing decisive quantitative and qualitative information. Such diagnostic capabilities find substantial utility in both research and industrial process environments. Therefore, an advancement in sensitivity, accuracy, or adaptability of the technique will have a significant impact.

Absorption is usually determined from measurement of a ratio of optical powers at a certain wavelength. Recently, a new technique, termed cavity ring-down spectroscopy (E. K Wilson, C&E News, Feb. 19, 1996, p. 34, incorporated herein by reference), has been developed to determine absorption by gases, which utilizes a pulsed light source and an optical cavity. Typically, a light pulse from a laser source is injected into a cavity which is formed by two high-reflectivity mirrors. The lifetime of the pulse in the cavity is highly sensitive to cavity losses, including absorption by gases. Measurement of the pulse decay time or "ring-down" time in the cavity can thereby provide a direct measure of absorption. Cavity ring-down eliminates the adverse effects of light source fluctuation, since the measurement is acquired with a single pulse of light. The feasibility of this technique arises from recent technological advances in optical polishing, which permit the fabrication of extremely low-scatter-loss optics. If ordinary optics such as high-reflectivity mirrors (R~99%)are used, the pulse lifetime in the cavity is too short for the cavity ring-down strategy to provide a significant improvement in sensitivity, as compared to conventional absorption methods. However, with the advent of superpolishing, such as that described in N. J. Brown, Ann. Rev. Mater. Sci. 16, p. 371 (1986), incorporated herein by reference, mirrors with 99.99% reflectivity or better can be fabricated to construct low-loss optical cavities, thereby permitting ultra-high sensitivity to be routinely realized. The cavity ring-down technique has thereby become a viable form of optical absorption metrology, with trace analysis capabilities that greatly exceed conventional absorption methods.

SUMMARY OF THE INVENTION

In accordance with the invention, a device is provided which permits the sensitive measurement of optical absorption by matter in any state with diffraction-limited spatial resolution through utilization of total internal reflection within a high-Q (high-quality, low-loss) optical cavity. Intra-cavity total reflection generates an evanescent wave that decays exponentially in space at a point external to the cavity, thereby providing a localized region where absorbing materials can be sensitively probed through alteration of the Q-factor of the otherwise-isolated cavity. When a light pulse is injected into the cavity and passes through the evanescent state, an amplitude loss resulting from absorption is incurred that reduces the lifetime of the pulse in the cavity. By monitoring the decay of the injected pulse, the absorption coefficient of matter within the evanescent wave region, is accurately obtained from the decay time measurement. In some embodiments of the invention, microsampling with high-spatial resolution is achieved through repeated refocussing of the light pulse at the sampling point, under diffraction-limited conditions.

In accordance with a preferred embodiment of the invention, an intra-cavity total reflection apparatus is provided for high sensitivity measurement of the optical absorption of a test material. The apparatus includes: injecting means for producing a light pulse of a switched continuous wave lightbeam; an optical cavity, including input and output reflecting surfaces and an interfacing surface, for providing total internal reflection of the light within the cavity so as to generate an evanescent wave at the totally reflecting surface which decays within a decay length outside of the cavity beyond the totally reflecting surface, the test material being disposed outside of the cavity within the decay length of the evanescent wave, and the injected light circulates between the input and output reflecting surfaces such that a portion of the injected light escapes from said cavity; and a measuring means disposed adjacent one of the reflecting surfaces for monitoring the portion of the injected light pulse that escapes from the cavity to determine the amount of time the light pulse takes to decay within the cavity.

In one particularly preferred embodiment the unitary structure includes a Pellin-Broca prism, the first reflecting surface includes a first highly reflective mirror, and the second reflecting surface includes a second highly reflective mirror, the first and the second highly reflective mirrors being disposed in a right angle configuration having an apex, the Pellin-Broca prism being located at said apex of said right angle configuration, the measuring means being disposed adjacent to the first highly reflective mirror, and the injecting means being disposed adjacent to the second highly reflective mirror.

In a second particularly preferred embodiment, the unitary structure includes a prism including first and second adjacent sides forming a ninety degree angle and the optical cavity further includes a highly reflective mirror positioned adjacent to the first side and constituting the first reflecting surface, the second side of the prism being coated with a highly reflective coating constituting the second reflecting surface, and the measuring means being disposed adjacent to the second side.

Advantageously the prism includes a third side constituting the interfacing surface, the first side includes an antireflective coating thereon and the second mirror includes a highly reflective coating thereon.

In a third particularly preferred embodiment, the reflecting surfaces are disposed in side by side relation and the unitary structure includes a retro-reflecting prism having a facing side facing the first and the second reflecting surfaces, an anti-reflective coating disposed on the facing side, and further sides for receiving the light pulse after passage thereof through the facing side and reflecting the light back through the facing side.

In a third embodiment, it is preferred that the test material is located adjacent one of the further sides and the measuring means is located adjacent the second reflecting surface.

Advantageously, the first and the second reflecting surfaces respectively comprise first and second highly reflective mirrors positioned adjacent the facing side.

In fourth particularly preferred embodiment, the unitary structure includes an optical element comprising first and second end faces and first and second spaced substantially parallel reflecting sides such that the injected light pulse enters the first end face, travels by internal reflection between the reflecting sides, and exits through the second end face, the first reflecting surface being located adjacent the first end face and the second reflecting surface being located adjacent the second face.

It is preferred that the first reflecting surface comprises a reflective mirror separate from said optical element and the second reflecting surface comprises a reflective coating on said second end face.

Advantageously, the measuring means is disposed adjacent to the reflective coating.

It is preferred that the injecting means comprises a laser. It is even more preferred that the laser comprises one of a pulsed-dye laser, a picosecond pulsed laser, and a femtosecond pulse laser.

In accordance with another aspect of the invention, a method for measuring the optical absorption of a material to be probed is provided. The method includes: injecting a light pulse or switched continuous wave light beam into a standing wave optical cavity at an angle sufficient to produce total internal reflection of the light within the cavity and to thereby generate an evanescent wave having a decay length outside of the optical cavity; and determining the optical absorption of the material to be probed by monitoring the decay time of the injected light within the optical cavity (i) with the material present within the decay length of the evanescent wave and (ii) with the material not present within the decay length of the evanescent wave, and by thereafter determining any change in the decay time of the injected light when the material is present as compared to when the material is not present.

In a preferred embodiment, the method further includes transverse mode matching the light before the injecting of the light.

Advantageously, the method further includes refocussing the injected light, and determining the optical absorption of the material to be probed again after the refocussing.

Other features and advantages of the invention will be set forth in, or apparent from, the following detailed description of the preferred embodiments of the invention.

DETAILED DESCRIPTION OF THE PREFERRED EMBODIMENTS

Figure 1:
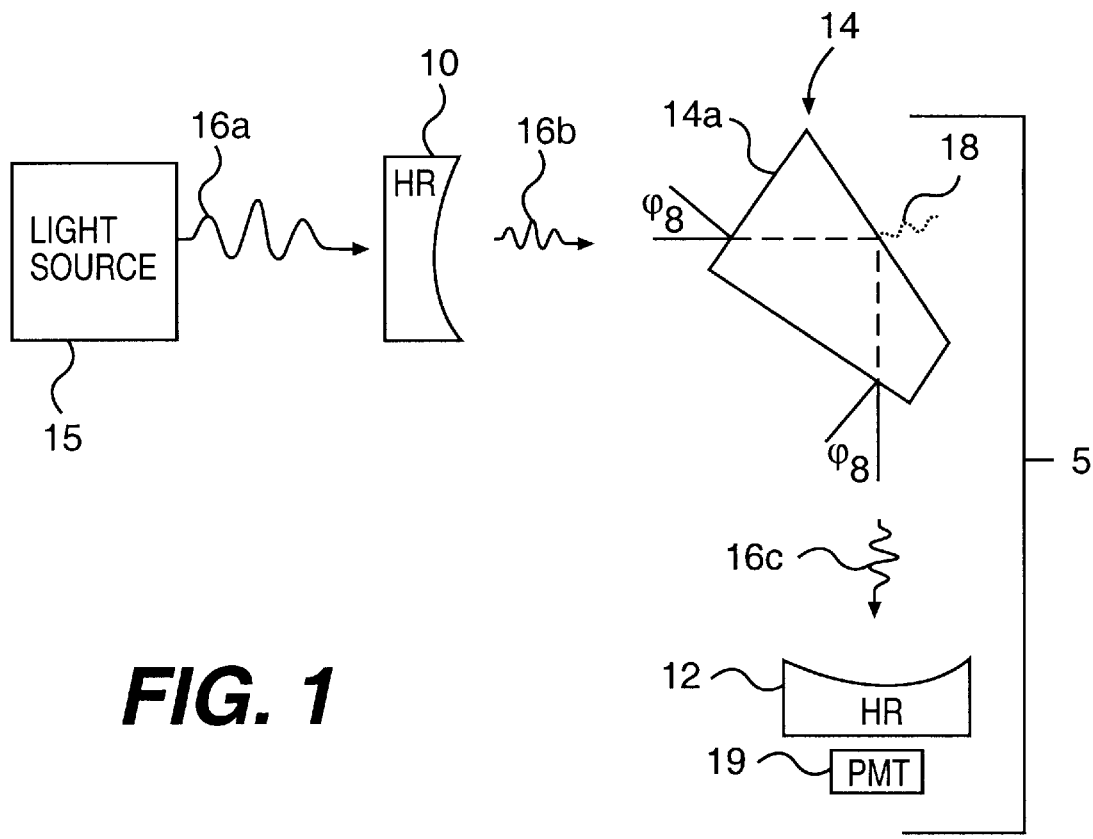
FIG. 1 is a schematic top elevational view of an optical cavity.

A further preliminary discussion is thought to be helpful at this point in fully understanding the invention. The measurement of optical absorption is fundamental to science and engineering, since an absorption spectrum provides a fingerprint which permits the qualitative and quantitative analysis of material composition. Absorption measurements are also frequently used to extract rates of chemical reactions and other processes. Key objectives in the development of a new technology for measurement of absorption are: 1) a reduction of the minimum detectable concentration, 2) an increase in the spatial resolution of the measurement, and 3) the incorporation of tunable, powerful, and highly monochromatic laser sources. By reducing the detection limit, important chemical reactions and processes that involve trace quantities or very short path lengths will be, in some cases, detectable for the first time or examined with higher signal-to-noise ratio thereby allowing more reliable quantification.

Previous attempts to increase the limit of detection have typically increased the sampled path length, which inherently results in a decrease in spatial resolution. A few devices have been developed which permit multiple sampling of a specific region, but typically with a small number of passes and a large beam diameter. The device of the present invention which uses a multiple-pass geometry with refocussing, substantially improves sensitivity and spatial resolution. Furthermore, by using a laser source with the device of the invention, the spatially coherent nature of laser light permits greater spatial resolution, since a focal spot size limited only by diffraction can be readily achieved. The laser-based device also benefits from the high output power and broad wavelength range obtainable through the combination of tunable, pulsed dye lasers and harmonic generation. Considering the current technological trend toward the micro- and nanostructured domains, the development of a sensitive absorption device with high-spatial resolution will likely facilitate technological innovations. However, to obtain the advantages of a pulsed laser source, the device circumvents the complication of pulse-to-pulse fluctuation, which is characteristic of pulsed laser systems. These measurements of optical absorption by intra-cavity total reflection achieve high-sensitivity with high-spatial resolution.

In the case of Attenuated Total Reflection (ATR) developed extensively by Harrick, *Internal Reflection Spectroscopy*, by N.J. Harrick (Interscience Publishers, New York 1967), incorporated herein by reference, an evanescent wave is generated by internal reflection in an optical cavity such as a prism, plate or thin-film waveguide at an internal angle of incidence that exceeds the critical angle. In ATR spectroscopy, the evanescent wave generated by total internal reflection at the base of a prism is used for optical absorption measurements by the conventional optical power ratio method. Absorption is determined from the optical power loss incurred in the critically reflected beam relative to total reflection when no absorbing material is present in the evanescent wave region.

ATR can be used to measure absorption for samples in the solid, liquid or gas phases, but is also highly effective for probing powders, fibers, thin-films, and absorbed molecular monolayers. For studies of thin-films and monolayers, ATR benefits from the enhanced surface electric field which exists at the interface where total reflection occurs. The direction of the surface field can also be controlled through polarization selection to probe molecular orientation effects, which can be important in, for example, catalysis and adhesion.

In optical cavity ATR, a light beam is coupled into a mode of an optical cavity, which contains an evanescent wave component that decays exponentially outside of the waveguide. Absorbing material within the decay length is then probed by measuring a corresponding power loss in the out-coupled beam after traversing the waveguide for a predetermined distance.

Waveguide cavity ATR has the advantage over ordinary ATR of increased effective path length, since light rays coupled into the cavity experience a large number of internal reflections over a short distance. The effective path length is proportional to the product of the total number of reflections and the evanescent wave decay length. However, conventional waveguide cavity ATR still employs an optical power ratio measurement, which ultimately limits its utility in trace analysis. In contrast, use of the monolithic, total internal reflection cavity in a cavity ring-down device like that discussed below eliminates the effect of source fluctuation, while achieving long effective path lengths through repeated circulation in addition to multiple reflections.

Although optical cavities have been described in many patents and publications, this does not detract from the originality of novel applications of such technology. For example, laser resonators and spectrum analyzers are common implementations of optical cavities, which in some cases use identical cavity designs.

The sensitivity of the measurement can be increased by utilizing optical element geometries that permit multiple total internal reflections and/or multiple passes to occur. Multiple reflections increase sensitivity with a concomitant decrease in spatial resolution by sampling at multiple points to yield an increase in the effective path length. A multiple-pass strategy repeatedly samples a single region to provide moderate spatial resolution. However, multiple pass elements typically provide only a few passes and do not refocus the beam at the sampled region to increase spatial resolution. Therefore, the development of an absorption technique which incorporates the powerful diagnostic capabilities of ATR and multiple-pass sampling with diffraction limited refocussing would represent a fundamental advancement in absorption measurement technology.

Apart from ATR is the cavity ring-down spectroscopy (CRDS) technique described in A. O'Keefe and D. A. G. Deacon, Rev. Sci. Instrum. 59, p. 2544 (1988) incorporated herein by reference, which is used for measuring the optical absorption spectra of gases. This technique was originally applied to narrowband gas phase absorption spectroscopy. U.S. Pat. No. 5,313,270 to Fishman and Haar, incorporated herein by reference, describes essentially identical technology to that of the O'Keefe reference mentioned above, with an intended application to the measurement of mirror reflectivity.

In CRDS, a single laser pulse is injected into a high-Q optical cavity, typically comprising a pair of concave high-reflectivity mirrors. Since the cavity Q-factor is high, the pulse makes many round trips, incurring only a small loss in amplitude per pass due to small intrinsic cavity losses resulting from, for example, mirror surface roughness scattering. Typically, the cavity is enclosed in a chamber which is filled with a gas of interest. When the frequency of the injected pulse corresponds to a resonant transition of the gas, the pulse amplitude loss per pass directly reflects the magnitude of the absorption. The temporal decay of the injected pulse is determined by monitoring the weak transmission which escapes from the cavity through one of the high-reflectivity mirrors. The transmitted intensity decays exponentially at a rate which reflects the total cavity losses, including absorption losses. Measurement of absorption is thereby achieved through a measurement of decay time instead of through a ratio of optical intensities. This time based measurement is equivalent to a large number of power ratio measurements with the same laser pulse, which inherently improves the accuracy and precision of the measurement since use of a single pulse eliminates the adverse effects of pulse-to-pulse fluctuation.

CRDS has only been applied to gas phase measurements, since the use of condensed matter sampling schemes which are common to transmission measurements, result in substantial intrinsic cavity losses which degrade the system performance. However, by utilizing intra-cavity total reflection, the advantages of a time-based absorption measurement can be combined with the advantages of ATR. The net result is a novel strategy for measurement of optical absorption by all states of matter. This strategy is fundamentally different from ATR, since a measurement of time instead of a ratio of intensities, is utilized. This strategy is different from CRDS since condensed matter can be probed through generation of an evanescent wave. Furthermore, the highly-localized nature of the evanescent wave combined with the spatial coherence provided by a laser source permits diffraction-limited spatial resolution and provides a decisively defined sample path length, which is necessary for accurate quantitative measurements.

Turning now to the embodiments shown in the drawings, which take advantage of the strategy discussed in the preceding paragraph, the illustrated devices are intra-cavity total reflection devices comprising a high-Q optical cavity formed by specially fabricated high reflectivity (~99.99%) mirrors and a totally reflecting optical element such as a prism. Losses introduced by any element in the system must be extremely small to produce a high-Q cavity.

It is noted that the preferred embodiments illustrated in FIGS. 1–4 use narrowband, multilayer coatings or Brewster's angle to achieve low cavity losses. In all of the embodiments disclosed, it is preferred that the optical cavities are stable optical cavities. Stable optical cavities are described in Lasers, by A. G. Seigman (University Science Books, California 1986), incorporated herein by reference.

In FIG. 1, a three element cavity 5 is formed by two high-reflectivity concave mirrors 10, 12 with equal radii of curvature, and a Pellin-Broca prism 14 in a right-angle configuration. A light source 15 for injecting light, described throughout as a laser, is positioned adjacent mirror 10, and a photomultiplier 19 is positioned adjacent mirror 12. The Pellin-Broca prism 14 provides a total internal reflection with very high internal transmission for a light beam 16a that is polarized in the plane formed by the three element cavity 5, since an incident beam 16b and an exiting beam 16c traverse the prism faces at the Brewster's angle $N_B$. By properly mounting the Pellin-Broca prism 14, the light beam will traverse the Pellin-Broca prism 14 at minimum deviation, which minimizes aberrations and beam translation with rotation about Brewster's angle $N_B$. Since the total internal reflection occurs at a hypotenuse surface 14a of the Pellin-Broca prism 14, an evanescent wave 18 decays exponentially into the region external to the hypotenuse surface 14a. Absorbing materials (not shown) placed within the decay length of the evanescent wave 18 can thereby be sensitively probed through the change in the decay time of a laser pulse injected into cavity 5. This decay time is detected by photomultiplier 19 which senses a very small portion of the injected light which escapes through mirror or reflector 12. Cavity losses for the configuration shown in FIG. 1 are largely determined by surface roughness induced scattering, although stress-birefringence of the Pellin-Broca prism 14 may induce polarization scrambling.

Figure 2:
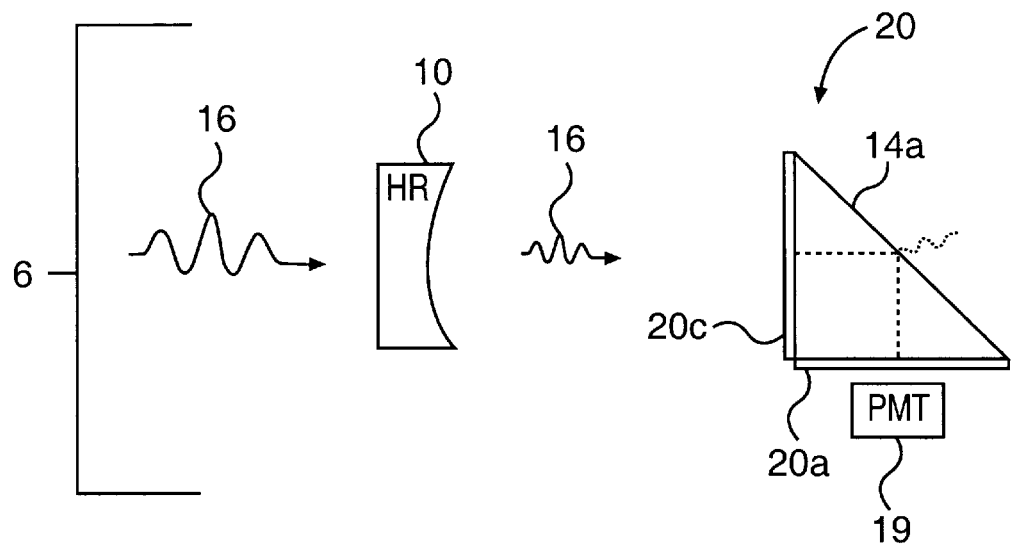
FIG. 2 is a schematic top elevational view of another embodiment of an optical cavity of the invention.

In FIG. 2, a two element cavity 6 is shown which comprising a single concave highly-reflective mirror or reflector 10 and a 90E prism 20. A first prism surface 20a of the prism 20 is coated with the same high reflective coating as is the concave reflector 10. Surface 20a is located at the beam waist of the concave reflector or mirror 10. Prism surface 14a is a totally reflecting surface where absorbing materials are probed. A further prism surface 20c must be anti-reflection coated over the design wavelength of cavity 6, to minimize losses resulting from the normal incidence of light beam 16, on surface 20c. The coating performance for surface 20c is a limiting source of loss for this cavity design, but unlike the design in FIG. 1, losses are independent of polarization. A photomultiplier detector 19 receives a small amount of light which passes through surface 20a. Since the evanescent wave 18 decay is in a region that is external to cavity 6 and is, in fact, external to the cavity for all embodiments depicted in FIGS. 1–4, the cavity can be sealed to protect the high-quality surfaces, thereby maintaining a high intrinsic cavity Q-factor. The sealed system can therefore be interfaced to a wide variety of external environments at the totally reflecting surface 14a.

Figure 3:
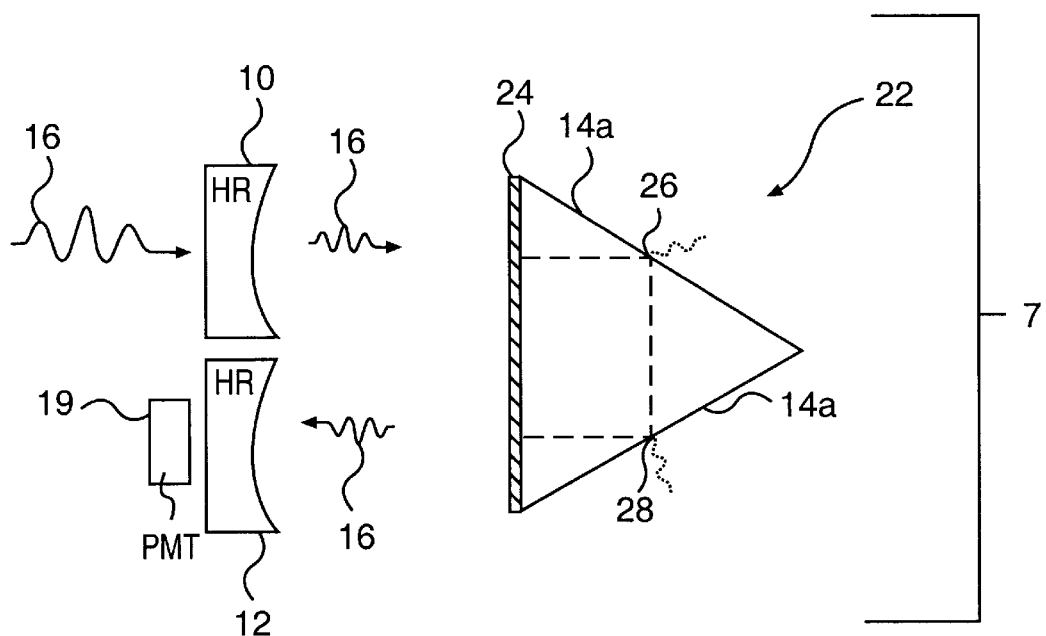
FIG. 3 is a schematic top elevational view of another embodiment of an optical cavity of the invention.
Figure 4:
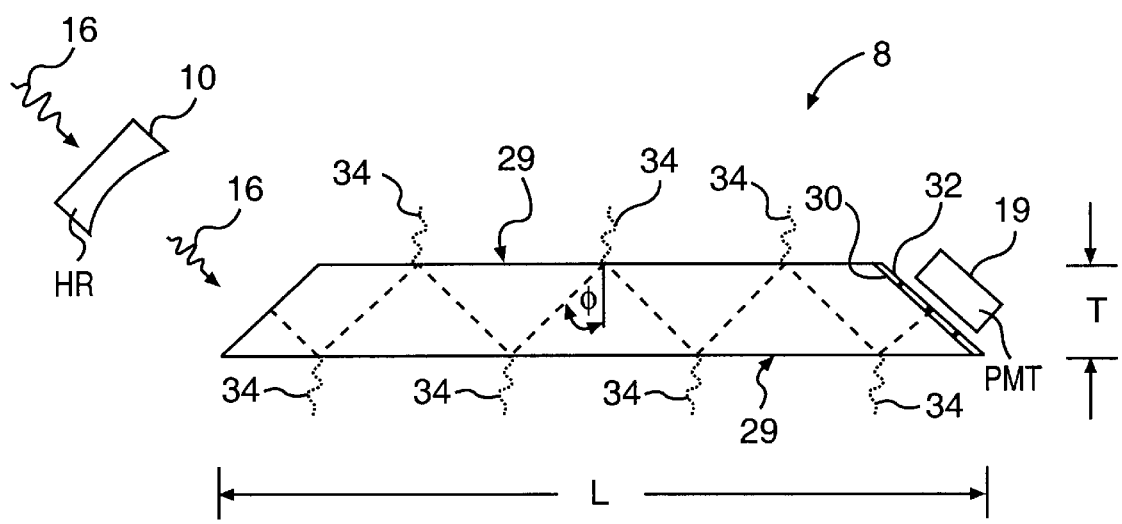
FIG. 4 is a schematic top elevational view of another embodiment of an optical cavity of the invention.

In the embodiment of FIGS. 3 and 4, cavities are provided multiple total internal reflective surfaces 14a as well as multiple passes. This enhances sensitivity by a factor equal to the number of total reflections, since as in ATR experiments the path length is increased. In FIG. 3, a cavity 7 is comprised of a retro-reflecting prism 22 and highly reflective mirrors 10, 12. While mirrors 10 and 12 are shown as two elements, they can be replaced by a single element. Retro-reflecting prism 22 has an anti-reflective coated surface 24 to minimize loss at normal incidence of beam 16, originating from laser 15, on surface 24. The beam waist is located approximately between two sampling points 26, 28, thereby providing high spatial resolution in addition to a factor of two gain in sensitivity. A photomultiplier 19 is disposed on the other side of mirror 12 and performs the detection function described above.

Referring to FIG. 4, a laser (not shown) is used to inject a light beam 16 into a cavity generally denoted 8 through a mirror 10. A seven-reflection, stable optical element 29 with a planar rear face 30 utilizes a high-reflectivity coating 32 on face 30 and the mirror 10 to form the cavity in this embodiment. Resultant evanescent waves 34 emanate from opposing surfaces of optical element 29 as spaced locations corresponding to the locations at which the beam 16 is reflected through these surfaces. A photomultiplier 19 performs the detecting function described above.

The number of reflections within the cavity can be controlled by varying the length, L, and thickness, T, of the element 29, according to, $$n = \left(\frac{L}{T}\right)\cot\theta$$

where $\Theta$ is the angle of incidence at the totally reflecting surface. The cavity design of FIG. 4 permits a substantial and controllable gain in sensitivity as compared to the designs of FIGS. 1–3.

The principles and applications of evanescent wave pulses in ATR absorption spectroscopy including the relationship between sensitivity, evanescent wave pulse decay length, angle of incidence, and refractive index difference across the totally reflecting boundary is further described in *Internal Reflection Spectroscopy*, by N. J. Harrick (*Interscience Publishers*, New York 1967) which was referred to above. The methods of ATR, including techniques for analysis of gases, liquids, solids, powders and thin films are directly applicable to diagnostics with the present invention. The mean angle of incidence for the totally reflected injected pulse is determined by the choice of cavity geometry, which for an N sided regular polygon is given by, $$\phi = \frac{\pi}{2}\left(1 - \frac{2}{N}\right) \quad (2)$$

The angle of incidence for all stable rays in the cavity must exceed the critical angle by, $$\theta_C = \text{SIN}^{-1}\left(\frac{n_2}{n_1}\right) \quad (3)$$

where the material composing the cavity is specified as medium $n_1$ and the medium to be measured which is surrounding the cavity is $n_2$. Sensitivity can be optimized for particular analysis conditions through the choice of angle of incidence and cavity material in accordance with the methods of ATR. Polarization dependent spectroscopy is also feasible, similar to ATR.

In general, it is important to note that although the cavity designs are quite simple, the surface quality required to produce a sufficiently high Q-factor necessitates the use of state-of-the-art polishing techniques, which can produce surfaces with <0.1 nm RMS surface roughness. Furthermore, these cavities form stable optical resonators, so that an injected light pulse will retrace its path in the cavity a large number of times. The beam waist associated with the stable mode of the cavity is located in the vicinity of the totally reflecting surface for designs in FIGS. 1–3 to optimize spatial resolution. The beam diameter at the waist is determined by the radius of curvature of the mirrors in the embodiments shown in FIGS. 1–4. In the embodiments of FIGS. 1 and 2, the sample is probed by the light pulse a number of times N, equal to the ratio of the decay time to one-half the round trip time. This value will typically be on the order of 1,000. For the embodiments of FIGS. 3 and 4, a sample can be probed N×n times, where n is the number of reflections.

Anticipated commercial applications for the invention include:
 1. Biosensor applications
 2. Catalysis
 3. Corrosion
 4. Adhesion
 5. Trace analysis
 6. Capillary electrophoresis detector
 7. Process measurements
 8. Optical constant determinations
 9. Hostile environments
 10. Trace analysis in general
 11. Research tool for surface science research Although the present invention has been described to specific exemplary embodiments thereof, it will be understood by those skilled in the art that variations in modifications can be effected in these exemplary embodiments without departing from the scope and spirit of the invention.

We claim:

1. An intra-cavity total reflection apparatus for high sensitivity measurement of the optical absorption of a test material, said apparatus comprising:
   injecting means for producing light for a predetermined length of time;
   an optical cavity, comprising first and second reflecting surfaces and an interfacing surface, for receiving said light produced by said injecting means and for providing total internal reflection of said light within said cavity so as to generate an evanescent wave at said interfacing surface which decays within a decay length outside of said cavity beyond said interfacing surface, said test material being disposed outside of said cavity within said decay length, and said injected light oscillates between said first and second reflecting surfaces such that a portion of said injected light escapes from said cavity; and measuring means disposed adjacent one of said reflecting surfaces for monitoring said portion of said injected light that escapes from said cavity to determine the amount of decay time said light takes to decay within said cavity and the optical absorption of said test material.

2. An apparatus as claimed in claim 1 wherein said interfacing surface comprises part of a unitary structure.

3. An apparatus as claimed in claim 1 wherein said measuring means comprises a photomultiplier.

4. An apparatus as claimed in claim 2 wherein said unitary structure comprises a Pellin-Broca prism, said first reflecting surface comprises a first highly reflective mirror, and said second reflecting surface comprises a second highly reflective mirror, said first and said second highly reflective mirrors being disposed in a right angle configuration having an apex, said Pellin-Broca prism being located at said apex of said right angle configuration, said measuring means being disposed adjacent to the first highly reflective mirror, and said injecting means being disposed adjacent to the second highly reflective mirror.

5. An apparatus as claimed in claim 2 wherein said unitary structure comprises a prism including first and second adjacent sides forming a ninety degree angle and said optical cavity further comprises a highly reflective mirror positioned adjacent to said first side and constituting said first reflecting surface, said second side of said prism being coated with a highly reflective coating constituting said second reflecting surface, and said measuring means being disposed adjacent to said second side.

6. An apparatus as claimed in claim 5 wherein said prism includes a third side constituting said interfacing surface.

7. An apparatus as claimed in claim 6 wherein said first side includes an antireflective coating thereon and said second mirror includes a highly reflective coating thereon.

8. An apparatus as claimed in claim 2 wherein said reflecting surfaces are disposed in side by side relation and said unitary structure comprises a retro-reflecting prism having a facing side facing said first and said second reflecting surfaces, an anti-reflective coating disposed on said facing side, and further sides for receiving said light after passage thereof through said facing side and reflecting said light back through said facing side.

9. An apparatus as claimed in claim 8 wherein the test material is located adjacent one of said further sides and said measuring means is located adjacent said second reflecting surface.

10. An apparatus as claimed in claim 8 wherein said first and said second reflecting surfaces respectively comprise first and second highly reflective mirrors positioned adjacent said facing side.

11. An apparatus as claimed in claim 8 wherein said first and said second reflecting surfaces are formed on a single element.

12. An apparatus as claimed in claim 2 wherein said unitary structure comprises an optical element comprising first and second end faces and first and second spaced substantially parallel reflecting sides such that said injected light enters said first end face, travels by internal reflection between said reflecting sides, and exits through said second end face, said first reflecting surface being located adjacent said first end face and said second reflecting surface being located adjacent said second face.

13. An apparatus as claimed in claim 12 wherein said first reflecting surface comprises a reflective mirror separate from said optical element and said second reflecting surface comprises a reflective coating on said second end face.

14. An apparatus as claimed in claim 13 wherein said measuring means is disposed adjacent to said reflective coating.

15. An apparatus as claimed in claim 1 wherein said injecting means comprises a laser.

16. An apparatus as claimed in claim 15 wherein said laser comprises one of a pulsed dye laser, a picosecond pulsed laser, a femtosecond pulses laser and a continuos wave laser.

17. An apparatus as claimed in claim 15 wherein said laser comprises a diode laser.

18. A method for measuring the optical absorption of a material to be probed, said method comprising:

injecting a light having a predetermined duration into a standing wave optical cavity at an angle sufficient to produce total internal reflection of said light within said cavity and to thereby generate an evanescent wave having a decay length outside of said optical cavity; and determining the optical absorption of the material to be probed by monitoring the decay time of said injected light within said optical cavity (i) with the material present within said decay length of said evanescent wave and (ii) with the material not present within said decay length of said evanescent wave, and by thereafter determining any change in the decay time of said injected light when said material is present as compared to when said material is not present.

19. A method as claimed in claim 18 further comprising transverse mode matching said light before said injecting of said light.

20. A method as claimed in claim 18 further comprising refocussing the injected light, and determining the optical absorption of the material to be probed again after said refocussing.

* * * * *